United States Patent [19]

Böshagen et al.

[11] Patent Number: 4,590,291

[45] Date of Patent: May 20, 1986

[54] THROMBIN INHIBITORY NEW DIHYDROXYBENZENE ETHER DERIVATIVES

[75] Inventors: Horst Böshagen, Haan; Ulrich Hörlein, Wuppertal; Gerd Reinhardt, Wuppertal; Friedel Seuter, Wuppertal; Elisabeth Perzborn, Wuppertal, all of Fed. Rep. of Germany

[73] Assignee: Bayer Aktiengesellschaft, Leverkusen, Fed. Rep. of Germany

[21] Appl. No.: 385,355

[22] Filed: Jun. 7, 1982

[30] Foreign Application Priority Data

Jun. 26, 1981 [DE] Fed. Rep. of Germany ....... 3125059

[51] Int. Cl.[4] .............................................. C07C 69/76
[52] U.S. Cl. ...................................... 560/64; 560/55;
562/473; 562/465; 562/587; 514/544; 514/532;
514/571; 514/568
[58] Field of Search ................. 560/64, 55; 562/473,
562/465; 568/648, 649; 514/544, 532, 571, 568

[56] References Cited

U.S. PATENT DOCUMENTS 3,998,874 12/1976 Nauta ................................. 568/649
4,351,950 9/1982 Sircar ................................. 560/62

FOREIGN PATENT DOCUMENTS

EP32063 7/1981 European Pat. Off. .
2921778 12/1979 Fed. Rep. of Germany .

Primary Examiner—Paul J. Killos
Attorney, Agent, or Firm—Sprung Horn Kramer & Woods

[57] ABSTRACT

An ether derivative of a dihydroxybenzene of the formula

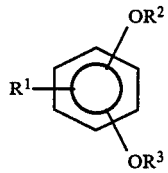

in which $R^1$ is 1 to 3 identical or different substituents selected from hydrogen, halogen, trifluoromethyl, carboxyl, alkyl, alkoxy, alkylmercapto and carbalkoxy, with in each case 1 to 4 carbon atoms in the alkyl and alkoxy groups, and $R^2$ and $R^3$ are different and each is an alkyl or alkenyl chain in which 1 or 2 $CH_2$ chain members are optionally replaced by O, S, CO or a phenylene group, and/or in which the chain is optionally substituted by 1 to 3 identical or different substituents selected from hydroxyl, halogen, trifluoromethyl, phenyl, carboxyl, alkyl, alkoxy, alkylmercapto, carbalkoxy, and acyl, the phenyl radical in turn optionally being substituted by halogen, trifluoromethyl, carboxyl, alkyl, alkoxy, alkylmercapto or carbaloxy, and the above-mentioned alkyl, alkoxy and acyl groups in each case containing 1 to 4 carbon atoms, and in which at least one of the radicals $R^2$ or $R^3$ is substituted and/or in at least one of the radicals $R^2$ or $R^3$ 1 or 2 chain members are replaced by 1 or 2 identical or different radicals selected from O, S, CO and phenylene, is effective in combating cardiac infarcations, angina pectoric, thromboembolic illnesses, in venous and arterial regions and arteriosclerosis.

10 Claims, No Drawings

THROMBIN INHIBITORY NEW DIHYDROXYBENZENE ETHER DERIVATIVES

The present invention relates to certain new dihydroxybenzene ether derivative compounds, to a process for their production and to their use as antithrombotic agents, in particular as thromboxan synthetase inhibitors and as thrombin inhibitors, and as antiatherosclerotic agents.

Dihydroxybenzene ethers and processes for their preparation are already known, (see, for example Beilst. 6, 771, 772, 814, 815, 843–846, Beilst. 6, Supplement I 383, 384, 402, 416, Beilst. 6, Supplement II 779–783, 813–816, 839 et seq., Beilst. 6, Supplement III 4205–4227, 4305–4319, 4385–4413, and Beilst. 6, Supplement IV 5564–5581, 5663–5672). No antithrombotic or antiatherosclerotic action of this class of substances has yet been described. Some dihydroxybenzene ether derivatives have been tested for action against coccidiosis, but no satisfactory actions have been found (see J.med.-Chem. 21, 357 (1978)).

According to the present invention we provide new compounds which are dihydroxybenzene ether derivatives of the general formula

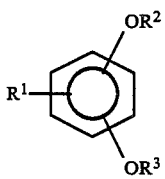
(I)

or a salt thereof, in which $R^1$ represents 1 to 3 identical or different substituents selected from hydrogen, halogen, trifluoromethyl, carboxyl, alkyl, alkoxy, alkylmercapto and carbalkoxy, with in each case 1 to 4 carbon atoms in the alkyl and alkoxy groups, and $R^2$ and $R^3$ are different and each represents a straight-chain or branched alkyl or alkenyl chain in which 1 or 2 $CH_2$ chain members are optionally replaced by O, S, CO or a phenylene group, and/or in which the chain is optionally substituted by 1 to 3 identical or different substituents selected from hydroxyl, halogen, trifluoromethyl, phenyl, carboxyl, alkyl, alkoxy, alkylmercapto, carbalkoxy, and acyl, the phenyl radical in turn optionally being substituted by halogen, trifluoromethyl, carboxyl, alkyl, alkoxy, alkylmercapto or carbalkoxy, and the abovementioned alkyl, alkoxy and acyl groups in each case containing 1 to 4 carbon atoms, and in which at least one of the radicals $R^2$ or $R^3$ is substituted and/or in at least one of the radicals $R^2$ or $R^3$ 1 or 2 $CH_2$ chain members are replaced by 1 or 2 identical or different radicals selected from O, S, CO and phenylene.

According to the present invention we further provide a process for the production of a compound of the present invention in which a hydroxybenzene derivative of the general formula

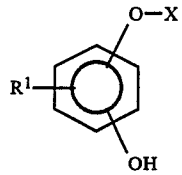
(II)

in which $R^1$ has the abovementioned meaning and
X represents a protective group, is reacted with a compound of the general formula $$Y-R^3 \quad (III)$$

in which $R^3$ has the abovementioned meaning and
Y represents a leaving group, in an inert organic aprotic solvent in the presence of an equivalent amount of a strong base at a temperature between 0° and 150° C., the protective group X is then split off, and the product is then etherified with a compound of the general formula $$Y'-R^2 \quad (IV)$$

in which $R^2$ has the abovementioned meaning and
Y' has the meaning of Y, but without having to be identical to this radical, under the reaction conditions specified above for the reaction of compounds of formulae (II) and (III), to give a compound of the general formula (I), which is converted, if desired, into a salt thereof.

Preferred protective groups as the substituent X which may be mentioned are acyl with 1 to 4 carbon atoms (in particular acetyl), benzoyl, benzyl, tetrahydropyranyl and trialkylsilyl with 1 to 4 carbon atoms in the alkyl radicals.

Preferred leaving groups as the substituent Y which may be mentioned are halogen (in particular chlorine and bromine), tolyl and alkylsulphonyl with 1 to 4 carbon atoms in the alkyl radical.

As preferred bases used as acid-binding agents in the reaction medium there may be mentioned alkali metal hydroxides, alkali metal hydrides, alkali metal amides, alkali metal alcoholates and butyl-lithium, particularly suitable alkali metals being sodium and potassium.

Preferred inert organic aprotic solvents which may be mentioned are toluene, benzene, dimethylformamide and dimethylsulphoxide, and mixtures of these solvents.

The reaction can be carried out under various pressures, preferably under normal pressure. It is carried out at a temperature between 0° and 150° C., in particular between 50° and 120° C.

As well as by the abovementioned preparation process, the compounds according to the invention can also be prepared by processes in which the alkylene or alkenylene chains of the substituents $R^2$ and $R^3$ are built up stepwise or varied by customary acylation, esterification, saponification or reduction processes. The possible acylation of hydroxyl substituents may be mentioned in particular.

A further possible variant which may be mentioned for the etherification of hydroxybenzene derivatives of formula (II) is the reaction with a terminally unsaturated compound of the general formula

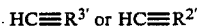

(Va)  (Vb)

in which

R[2]' and R[3]' correspond to the radicals R[2] and R[3] defined above, the chain length of these substituents in each case being shortened by 2 carbon atoms.

If desired, the alkylene ethers thereby obtained can be converted into the corresponding alkyl ethers by hydrogenation.

The dihydroxybenzene derivatives of the general formula (II) which can be used according to the invention and the compounds of the general formulae (III) and (IV) can be prepared by known methods (see the literature references from Beilstein 6 mentioned above).

Examples of radicals R[3], attached to leaving groups Y in compounds of the general formula (III), which may be mentioned are: 3-oxo-1-(E)-octenyl, 3-oxo-octyl, 3-hydroxy-1-(E)-octenyl, 3-hydroxy-octyl, 3-acetoxy-1-(E)-octenyl, 3-acetoxy-octyl, 3-oxo-1-(E)-nonenyl, 3-oxo-nonyl, 3-hydroxy-1-(E)-nonenyl, 3-acetoxy-nonyl, 3-oxo-1-(E)-heptenyl, 3-oxo-heptyl, 3-acetoxy-1-(E)-heptenyl, 3-acetoxy-heptyl, 4-(4-methoxyphenyl)-oxybutyl, 4-(3-methoxyphenyl)-oxybutyl, 3-(4-methoxyphenyl)-oxypropyl, 3-(3-methoxyphenyl)-oxypropyl, 4-(2-methoxyphenyl)-oxy-butyl, 3-(2-methoxyphenyl)-oxypropyl, 4-(4-chlorophenyl)-oxybutyl, 4-(3-chlorophenyl)-oxybutyl, 3-(4-chlorophenyl)-oxypropyl, 3-(3-chlorophenyl)-oxypropyl, 4-(2-chlorophenyl)-oxybutyl, 3-(2-chlorophenyl)-oxypropyl, 4-oxo-2-octyl, 4-oxo-2-nonyl, 4-oxo-2-decyl, 4-oxo-2-undecyl, 4-hydroxy-2-octyl, 4-hydroxy-2-nonyl, 4-hydroxy-2-decyl, 4-hydroxy-2-undecyl, 4-(4-methoxyphenyl)-oxy-2-(E)-butenyl, 4-(3-chlorophenyl)-oxy-2-(E)-butenyl, 4-(3-methoxyphenyl)-oxy-2-(E)-butenyl, 4-(2-methoxyphenyl)-oxy-2-(E)-butenyl, 4-(4-chlorophenyl)-oxy-2-(E)-butenyl, 4-(2-chlorophenyl)-oxy-2-(E)-butenyl, 4-(4-carboxyphenyl)-oxybutyl, 4-(4-carboxyphenyl)-oxy-2-(E)-butenyl, 4-(4-methoxyphenyl)-thiobutyl, 4-(3-methoxyphenyl)-thiobutyl, 4-(2-methoxyphenyl)-thiobutyl, 4-(4-chlorophenyl)-thiobutyl, 4-(3-chlorophenyl)-thiobutyl, 4-(2-chlorophenyl)-thiobutyl, 4-(4-methoxyphenyl)-thio-2-(E)-butenyl, 4-(3-methoxyphenyl)-thio-2-(E)-butenyl, 4-(2-methoxyphenyl)-thio-2-(E)-butenyl, 4-(4-chlorophenyl)-thio-2-(E)-butenyl, 4-(3-chlorophenyl)-thio-2-(E)-butenyl, 4-(2-chlorophenyl)-thio-2-(E)-butenyl, 4-hydroxy-5-(3-trifluoromethyl-phenoxy)-2-(E)-pentenyl, 4-hydroxy-5-(4-chlorophenoxy)-2-(E)-pentenyl, 4-(3-methyl-phenyl)-oxy-3-hydroxy-1-(E)-butenyl, 4-(3-methylphenyl)-thio-3-hydroxy-1-(E)-butenyl, [3-(4-hydroxybutyl)-phenyl]-methyl, [3-(5-hydroxypentyl)-phenyl]-methyl, [3-(3-hydroxypropyl)-phenyl]-methyl, [4-(4-hydroxybutyl)-phenyl]-methyl, [4-(5-hydroxypentyl)-phenyl]-methyl, 3-[(4-methyl-thiomethyl)-phenyl]-3-methyl-3-hydroxy-1-(E)-propenyl and e-[(3-ethylthiomethyl)-phenyl]-3-ethyl-3-hydroxy-1-(E)-propenyl.

Examples of radicals R[2], attached to leaving groups Y' in compounds of the general formula (IV), which may be mentioned are: 1-carbomethoxy-hexyl, 1-carbethoxy-hexyl, 1-carboxy-hexyl, 1-carbomethoxy-5-hydroxy-hexyl, 1-carbethoxy-5-hydroxy-hexyl, 1-carboxy-5-hydroxy-hexyl, 1-carbomethoxy-4-(Z)-hexenyl, 1-carbethoxy-4-(Z)-hexenyl, 1-carboxy-4-(Z)-hexenyl, 1-carbomethoxy-4-(E)-hexenyl, 1-carbethoxy-4-(E)-hexenyl, 1-carboxy-4-(E)-hexenyl, 3-(4-carbomethoxyphenyl)-propyl, 3-(4-carbethoxyphenyl)-propyl, 3-(4-carboxyphenyl)-propyl, 3-(3-carbomethoxyphenyl)-propyl, 3-(3-carbethoxyphenyl)-propyl, 3-(3-carboxyphenyl)-propyl, 4-(ω-carbethoxystyryl)-methyl, 4-(ω-carbomethoxystyryl)-methyl, 4-(ω-carboxystyryl)-methyl, 3-(ω-carbethoxystyryl)-methyl, 3-(ω-carboxystyryl)-methyl, 3-(ω-carbomethoxystyryl)-methyl, 2-(ω-carbethoxystyryl)-methyl, 2-(ω-carbomethoxystyryl)-methyl, 2-(ω-carboxystyryl)-methyl, 4-[(2-carbethoxyethyl)-phenyl]-methyl, 4-[(2-carbomethoxyethyl)-phenyl]-methyl, 4-[(2-carboxyethyl-phenyl)]-methyl, 3-[(2-carbethoxyethyl)-phenyl]-methyl, 3-[(2-carbomethoxyethyl)-phenyl]-methyl, 3-[(2-carboxyethyl)-phenyl]-methyl, 2-[(2-carbethoxyethyl)-phenyl]-methyl, 2-[(2-carbomethoxyethyl)-phenyl]-methyl and 2-[(2-carboxyethyl)-phenyl]-methyl.

Particularly preferred compounds according to the present invention are those in which R[1] represents a hydrogen, fluorine or chlorine atom, a carboxyl, methyl or methoxy group or a carbalkoxy group with 1 to 4 carbon atoms in the alkoxy group and R[2] and R[3] are different and represent a straight-chain or branched alkyl or alkenyl chain with up to 16 carbon atoms in which 1 or 2 $CH_2$ chain members are optionally replaced by O, CO or phenylene, and/or which is optionally substituted by 1 to 3 substituents selected from hydroxyl, fluorine, chlorine, bromine, trifluoromethyl, phenyl, carboxyl, alkyl with 1 or 2 carbon atoms, alkoxy with 1 or 2 carbon atoms, methylmercapto, carbalkoxy with 1 or 2 carbon atoms in the alkoxy radical and acetyl, the phenyl radical in turn optionally being substituted by fluorine, chlorine, bromine, trifluoromethyl, carboxyl, methyl, ethyl, methoxy, methylmercapto, carbomethoxy or carbethoxy, and wherein at least one of the radicals R[2] or R[3] is substituted and/or in at least one of the radicals R[2] or R[3] 1 or 2 $CH_2$ chain members are replaced by 1 or 2 identical or different radical selected from O, CO and phenylene.

The reagents required for introducing the radicals R[2] and R[3] can be prepared by processes which are known from the literature. Examples which may be mentioned are: Chem. Abstr. 89, 108697j (1978), Chem. Abstr. 89, 157299q (1978), Chem Abstr. 90, 38693z (1979), Chem. Abstr. 90, 186463q (1979), DOS (German Published Specification) No. 2,822,156, DOS (German Publishing Specification) No. 2,323,193 and U.S. Pat. No. 4,211,884.

The compounds according to the present invention can be used if blood platelet aggregation is to be prevented, the glutinous properties of platelets are to be reduced and the formation of blood clots (thrombi) is to be prevented (prophylaxis of thrombosis). The thrombin inhibition found in the compounds according to the invention can likewise inhibit or prevent thrombi formation (prophylaxis of thrombosis). An additional property of the compounds according to the present invention is the inhibition of thromboxan synthesis, whereupon the formation of thromboxan ($TXA_2$), which triggers off platelet aggregation and has a vasoconstricting action is prevented. In experimental atherosclerosis models, the compounds also inhibit the proliferation of vessel intima which is triggered off by injury and hyperlipidaemia and is regarded as an early stage of atherosclerotic changes.

The following test methods demonstrate the surprising action of the compounds according to the present invention:

1. Determination of the antiarteriosclerotic action

A section of the carotid artery in rats was exposed by surgery and cooled to −10° C. After the operation, the animals were fed with a cholesterol-rich diet for 10 days. Atherosclerotic deposits thereby formed in the damaged vessel, the extent of these deposits being determined histologically or by weighting. (See F. Seuter et al., "Experimentally induced Thromboatherosclerosis in rats and rabbits", Folia Angiologica 28, 85–87 (1980)).

It was found that, for example, formation of the deposits was inhibited by 59% on oral administration of a dose of 100 mg/kg of the compound of Example 10.

2. Inhibition of thrombin

Doses of 1 to 50 μl of the substances to be investigated were initially introduced into a test tube and the quantities were made up with buffer. 20 μl of thrombin solution were added to the batches, and the batches were left to stand at room temperature for 20 minutes. The reaction was then initiated by means of a substrate solution. The rise in extinction per minute was determined, as a measure of the activity. It was found that, for example, the minimum threshold concentration of inhibition is 2 μg/ml for the compound of Example 24. Numerous compounds according to the invention displayed inhibition at a dose of 10 to 20 μg/ml.

3. Inhibition of thromboxan synthesis

Some of the compounds according to the invention have a very specific inhibiting action on thromboxan synthetase, without having a greater influence on cyclooxygenase. The compound of Example 8 inhibited thromboxan synthetase by 86% even in a concentration of $3 \times 10^{-5}$ g/ml. At the same dose, the compound of Example 12 showed an inhibition of 96%. The investigations were carried out analogously to known test methods (see R. F. Furchgott et al., Pharmakol, Exp. Ther. 108, 129–143 (1953) and J. M. Bailey et al., Prostaglandins 13, 479–492 (1977)).

On the basis of the abovementioned action qualities, the compounds according to the invention are suitable, for example, for the treatment or prevention of cardiac infarctions, angina pectoris, thromboembolic illnesses in the venous and arterial region (post-operative, transitory ischaemic attacks, amaurosis fugax and the like), and of other vascular symptoms, such as arteriosclerosis.

As stated above, the invention also relates to the use in human and veterinary medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the abovementioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitan esters), microcrystalline cellulose, aluminum metahydroxide, bentonite, agar-agar and tragacanth or mixtures thereof.

All the pharmaceutical compositions according to the invention can also contain coloring agents and preservatives as well as perfumes and flavoring additions (e.g. peppermint oil and eucalyptus oil) and sweetening agents (e.g. saccharine).

The pharmaceutical compositions according to the invention generally contain from 0.5 to 90% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention.

Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampules. Some of these forms may be made up for delayed release of the active ingredient. Some, such as capsules, include a protective envelope which renders the portions of the medicament physically discrete and coherent.

The preferred daily dose for intravenous administration of the medicaments of the invention is 2.5 to 250 mg of active ingredient and for oral administration of the medicaments of the invention is 25 to 250 mg of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally or parenterally, especially perlingually or intravenously. Preferred pharmaceutical compositions and medicaments are therefore those adapted for administration such as oral or parenteral administration. Administration in the method of the invention is preferably oral or parenteral administration.

In general it has proved advantageous to administer parenterally amounts of from 0.01 to 10 mg/kg, preferably 0.05 to 5 mg/kg, of body weight per day or to administer orally amounts of from 0.05 to 20 mg/kg, preferably 0.5 to 5 mg/kg of body weight per day, to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some cases suffice to use less than the above-mentioned minimum dosage rate, while in other cases the upper limit mentioned must be exceeded to achieve the desired results. Where larger amounts are administered it can be advisable to divide these into several individual administrations over the course of the day.

The following examples illustrate processes for the production of compounds of the present invention.

EXAMPLE 1

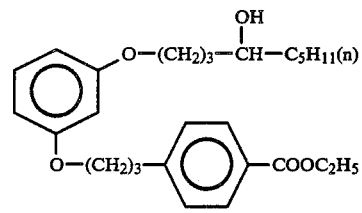

(a) A solution of 20.2 g of technical grade Euresol (O-monoacetylresorcinol) in 40 ml of a 1:1 benzene/dimethylformamide mixture dried over a molecular sieve was added dropwise to a suspension of 3.33 g of NaH (80% in paraffin) in 180 ml of the said solvent mixture. A trace of NaI was added and the mixture was heated to the boiling point. 29.5 g of 4-acetoxy-1-nonyl chloride were now added dropwise and the mixture was allowed to boil for 15 hours. After being cooled, the mixture was filtered with suction, the filtrate was concentrated in vacuo, the residue was taken up in ether and the ethereal solution was washed with water and dried over $Na_2SO_4$. After filtration, the evaporation residue was distilled. Yield: 23 g of Euresol 4-acetoxy-nonyl ether of boiling point $_{0.1}$ 195° to 200° C.

(b) 22 g of Euresol 4-acetoxy-nonyl ether were hydrolyzed by boiling for several hours in a mixture of 35 ml of 33% strength sodium hydroxide solution, 65 ml of water and 200 ml of ethanol. After being cooled, the solution was evaporated in vacuo, the residue was taken up in water, the solution was filtered with suction, using charcoal/"Tonsil" (Trade Mark) and the filtrate was rendered acid with hydrochloric acid. The 4-hydroxy-nonyl resorcyl ether which had separated out was taken up in ether, the ethereal solution was washed with water, dried over Na$_2$SO$_4$ and filtered and the filtrate was completely evaporated in vacuo. The residue weighed 16.5 g.

(c) A solution of 16 g of 4-hydroxy-nonyl resorcyl ether in 40 ml of a 1:1 benzene/dimethylformamide mixture treated as above was added dropwise to a suspension of 2.4 g of NaH (80% in paraffin) in 120 ml of the said solvent mixture. A trace of NaI was added and the mixture was heated to the boiling point. 17.45 g of 4-(3-bromopropyl)-benzoic acid ethyl ester were then added dropwise and the mixture was allowed to boil for 15 hours. After being cooled, the mixture was filtered with suction, the filtrate was completely concentrated in vacuo, the residue was partitioned between dilute sodium hydroxide solution and ether and the ethereal solution was dried over Na$_2$SO$_4$ and evaporated. Distillation of the residue in a retort flask with wide cross-sections gave 22 g of the ester of the above formula of boiling point $_{0.01}$ 262° to 267° C.

EXAMPLE 2

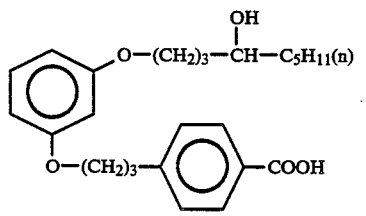

17.7 g of the ester from Example 1 were boiled with 15 g of NaOH in a mixture of 60 ml of water and 150 ml of ethanol for some hours. After being cooled, the mixture was evaporated in vacuo, the residue was taken up in water and the resulting solution was filtered with suction, using charcoal/"Tonsil" (Trade Mark). Acidification with hydrochloric acid gives the acid of the above formula, which, when recrystallized from ether/petroleum ether, had a melting point of 87° C. Yield: 12.7 g.

EXAMPLE 3

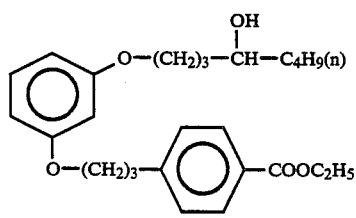

If Euresol was reacted with 4-acetoxy-1-octyl chloride analogously to Example 1, the hydrolysis of the acetyl groups was carried out as described and the resorcyl ether isolated was reacted with 4-(3-bromopropyl)-benzoic acid ethyl ester, the ester of the above formula of boiling point $_{0.01}$ 258° to 260° C. (retort flask with wide cross-sections) was obtained, with the appropriate corresponding yields.

EXAMPLE 4

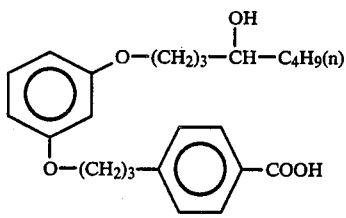

17.1 g of the ester from Example 3 were boiled with 15 g of NaOH in a mixture of 60 ml of water and 150 ml of ethanol for some hours. Working up analogously to Example 2 gave the acid of the above formula of melting point 90° to 91° C. (ether/petroleum ether). Yield: 11.5 g

EXAMPLE 5

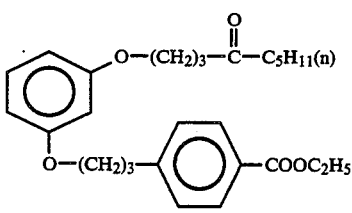

5.7 g of the ester from Example 1 were left to stand with 20.8 g of pyridine/chromium trioxide in 140 ml of methylene chloride for 20 minutes. The mixture was then filtered, with the addition of animal charcoal, and the methylene chloride solution was washed three times with dilute hydrochloric acid and then with sodium bicarbonate solution. The methylene chloride solution was evaporated in vacuo and the last traces of methylene chloride were driven off with steam. The residue was then extracted with ether, the ethereal solution was clarified with "Tonsil" (Trade Mark)/animal charcoal and the ether was driven off completely, finally under 3 to 5 mm Hg/120° C. Yield of keto ester of the above formula: 3.9 g

EXAMPLE 6

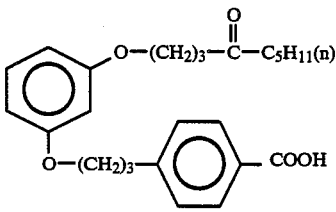

6.3 of the keto ester from Example 5 were boiled with 2.35 g of NaOH in a mixture of 15 ml of water and 45 ml of water and 45 ml of ethanol for 4 to 5 hours. A little water was then added and the solution was evaporated in vacuo. The sodium salt was dissolved in water, and the solution was purified by filtration with suction, using charcoal, and acidified. The acid of the above formula which had been filtered off with suction and dried was recrystallized from ether/petroleum ether. Yield: 4.0 g of melting point 82.5° to 84° C.

EXAMPLE 7

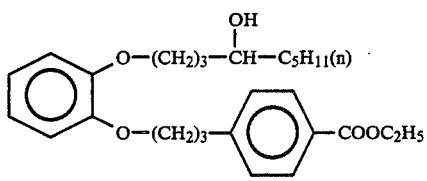

(a) A solution of 30.9 g of technical grade O-monoacetylpyrocatechol in 80 ml of benzene was added dropwise to a suspension of 6.7 g of NaH (80% in paraffin) in 30 ml of benzene, a trace of NaI was added, 100 ml of dry dimethylformamide were added, and 50.5 g of 4-acetoxynonyl chloride were added dropwise at the boiling point. The mixture was allowed to boil for 15 hours, cooled and filtered with suction and the filtrate was evaporated in vacuo. The residue was taken up in ether, the ethereal solution was washed with a solution of sodium bicarbonate in water, dried ($Na_2SO_4$) and evaporated and the evaporation residue was distilled. Yield: 36.8 g of O-acetylpyrocatechol 4-acetoxy-nonyl ether of boiling point $_{0.01}$ 182° to 184° C.

(b) 36 g of O-acetylpyrocatechol 4-acetoxy-nonyl ether were boiled in a solution of 32.6 g of NaOH in 200 ml of water and 350 ml of alcohol for several hours. The solution was then evaporated in vacuo, the residue is partitioned between ether and water, the ethereal solution was washed with water, dried ($Na_2SO_4$) and filtered and the filtrate was completely evaporated in vacuo. Yield of pyrocatechol 4-hydroxy-nonyl ether: 25.6 g.

(c) 25 g of pyrocatechol 4-hydroxy-nonyl ether were reacted with 27.0 g of 4-(3-bromopropyl)-benzoic acid ethyl ester in the presence of 3.75 g of NaH (80% in paraffin) as described in Example 1c), and the mixture was worked up in a corresponding manner. The ester of the above formula crystallized on trituration with petroleum ether. Yield: 41.3 g of melting point 53° to 54° C.

EXAMPLE 8

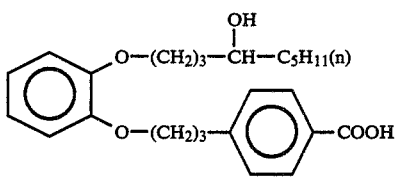

If the ester of Example 7 was hydrolyzed analogously to Example 2, the above acid of melting point 89° to 90° C. (ether/petroleum ether) was obtained.

EXAMPLE 9

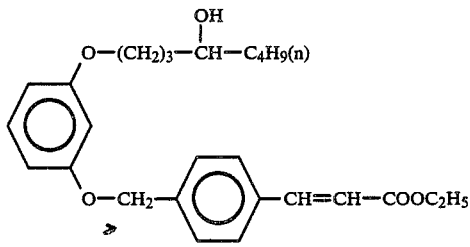

If 4-hydroxy-octyl resorcyl ether (intermediate of Example 3) was reacted with (4-α-bromoethyl)-(E)-cinnamic acid ethyl ester analogously to Example 1c), the above ester of boiling point $_{0.01}$ 228° to 230° C. (retort flask with wide cross-sections) was obtained in a yield corresponding to Example 1c).

EXAMPLE 10

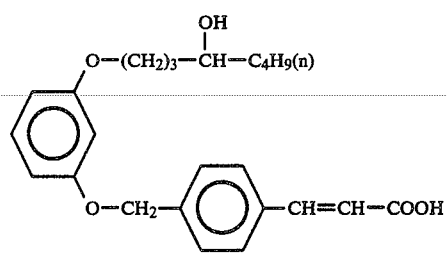

If the ester of Example 9 was hydrolyzed analogously to Example 4, the above acid of melting point 118° to 119° C. (cyclohexane) was obtained.

EXAMPLE 11

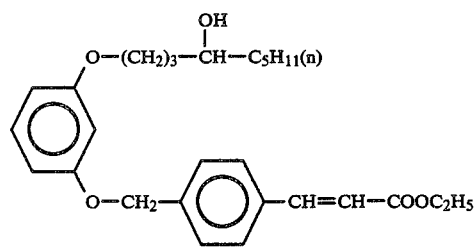

If 4-hydroxy-nonyl resorcyl ether (Example 1b)) was reacted with (4-α-bromomethyl)-(E)-cinnamic acid ethyl ester analogously to Example 1c), the above ester of boiling point $_{0.01}$ 230° to 232° C. (retort flask with wide cross-sections) was obtained in a yield corresponding to 1c).

EXAMPLE 12

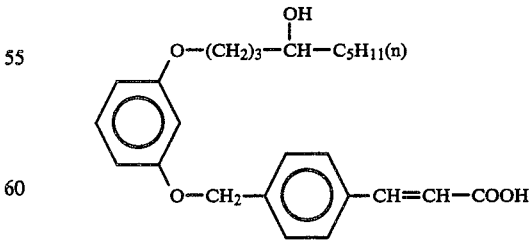

If the ester of Example 11 was hydrolyzed analogously to Example 4 (boiling time of 30 minutes), the above acid was obtained in a very good yield. Melting point: 115° C. (ethyl acetate/ether).

EXAMPLE 13

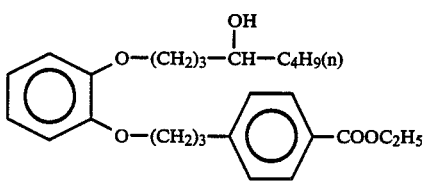

If O-monoacetyl-pyrocatechol was reacted with 4-acetoxy-1-octyl chloride analogously to Example 7, the hydrolysis of the acetyl groups was carried out as described and the pyrocatechol ether isolated was reacted with 4-(3-bromopropyl)-benzoic acid ethyl ester, the ester of the above formula of boiling point $_{0.01}$ 225° to 230° C. was obtained with good yields.

EXAMPLE 14

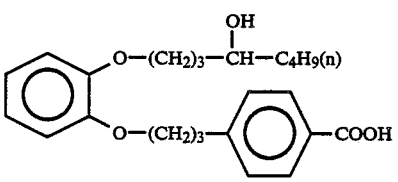

If the ester from Example 13 was hydrolyzed analogously to Example 12, the above acid was obtained in a very good yield. Boiling point: 69° to 70° C. (ether/petroleum ether).

EXAMPLE 15

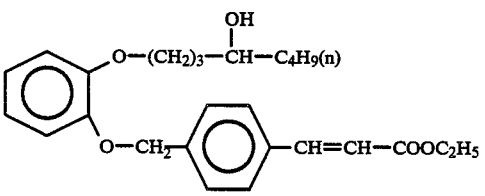

If pyrocatechol 4-hydroxy-octyl ether (intermediate from Example 13) was reacted with (4-α-bromomethyl)-(E)-cinnamic acid ethyl ester analogously to Example 7, the above ester was obtained in a good yield. Melting point: 56° to 57° C. (after trituration with petroleum ether).

EXAMPLE 16

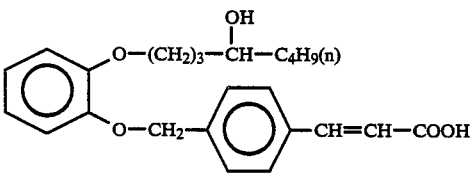

If the ester from Example 15 was hydrolyzed analogously to Example 12, the above acid was obtained in a very good yield. Melting point: 110° to 111° C. (a little ether/petroleum ether).

EXAMPLE 17

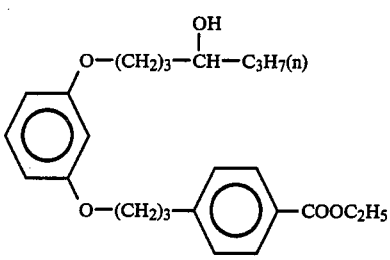

If Euresol was reacted with 4-acetoxy-heptyl chloride analogously to Example 1, the hydrolysis of the acetyl groups was carried out as described and the resorcyl ether isolated was reacted with 4-(3-bromopropyl)-benzoic acid ethyl ester, the ester of the above formula of boiling point $_{0.01}$ 240° to 245° C. was obtained, in the appropriate corresponding yields.

EXAMPLE 18

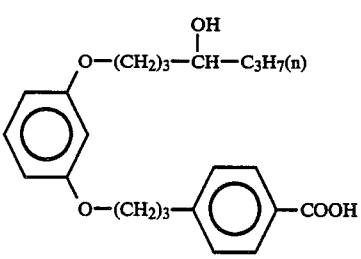

If the ester from Example 17 were hydrolyzed analogously to Example 12, the above acid was obtained in a good yield. Melting point: 84° to 85° C. (toluene/petroleum ether).

EXAMPLE 19

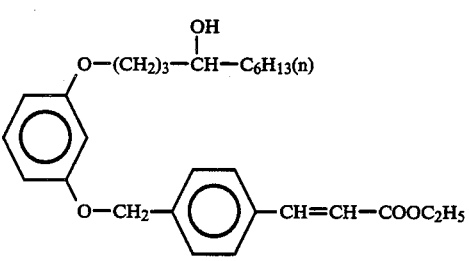

If the Euresol was reacted with 4-acetoxy-decyl chloride analogously to Example 1, the hydrolysis of the acetyl groups was carried out as described and the resorcyl ether isolated was reacted with (4-α-bromomethyl)-(E)-cinnamic acid ethyl ester, the ester of the above formula of boiling point $_{0.01}$ 232° to 235° C. and melting point 49° to 50° C. (trituration with petroleum ether) was obtained, in the appropriate corresponding yields.

EXAMPLE 20

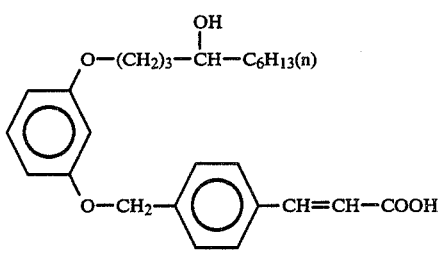

If the ester from Example 19 was hydrolyzed analogously to Example 12, the above acid was obtained in a good yield. Melting point: 122° to 124° C. (methyl acetate/petroleum ether).

EXAMPLE 21

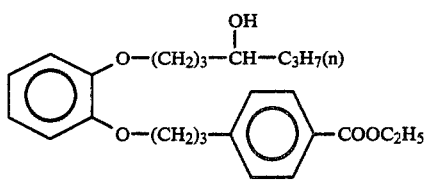

If O-monoacetyl-pyrocatechol was reacted with 4-acetoxy-heptyl chloride analogously to Example 7, the hydrolysis of the acetyl groups was carried out as described and the pyrocatechol ether isolated was reacted with 4-(3-bromopropyl)-benzoic acid ethyl ester, the ester of the above formula was obtained in a good yield. Boiling point $_{0.01}$ 224° to 227° C.

EXAMPLE 22

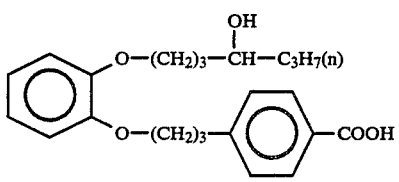

If the ester from Example 21 was hydrolyzed analogously to Example 12, the above acid was obtained. Melting point: 68° to 69° C. (cyclohexane).

EXAMPLE 23

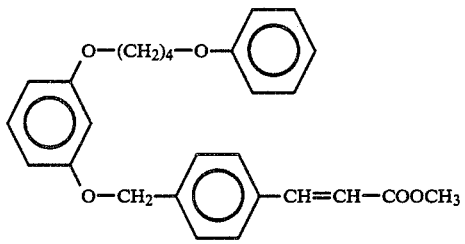

If Euresol was reacted with 4-phenoxy-butyl bromide analogously to Example 1, the hydrolysis of the acetyl group was carried out as described and the resorcyl ether isolated was reacted with (4-α-bromomethyl)-(E)-cinnamic acid methyl ester, the ester of the above formula of melting point 77° to 78° C. (methanol) was obtained, in the appropriate corresponding yields.

EXAMPLE 24

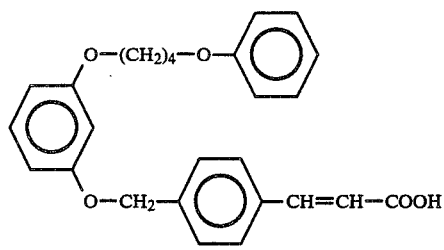

If the ester from Example 23 was hydrolyzed analogously to Example 12, using methanol instead of ethanol, the above acid was obtained. Melting point: 161° C. (methanol).

EXAMPLE 25

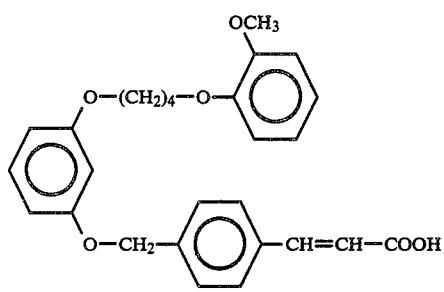

If Euresol was reacted with [(2-methoxy)-4-phenoxy]-butyl bromide analogously to Example 1, the hydrolysis of the acetyl group was carried out as described and the resorcyl ether isolated was reacted with (4-α-bromomethyl)-(E)-cinnamic acid methyl ester, the methyl ester of the above acid was obtained. This was hydrolyzed, as the crude product, analogously to Example 24. Melting point: 123° to 124° C. (methanol).

EXAMPLE 26

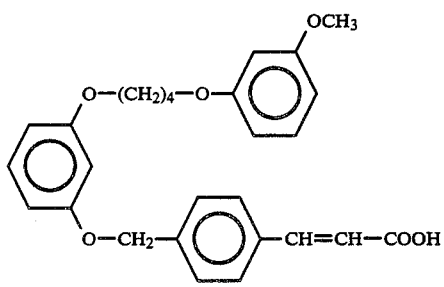

If Euresol was reacted with [(3-methoxy)-4-phenoxy]-butyl bromide analogously to Example 1, the hydrolysis of the acetyl group was carried out as described and the resorcyl ether isolated was reacted with (4-α-bromomethyl)-(E)-cinnamic acid methyl ester, the methyl ester of the above acid was obtained. This was hydrolyzed, as a crude product, analogously to Example 24. Melting point: 155° to 156° C., (methanol).

EXAMPLE 27

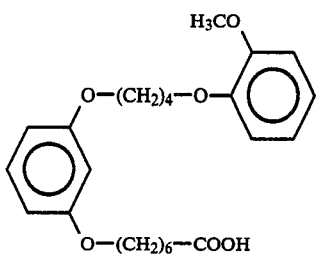

If [(2-methoxy)-4-phenoxy]-butyl resorcyl ether, an intermediate from Example 25, was reacted with 7-bromoheptanoic acid methyl ester analogously to Example 1c), the methyl ester of the above acid was obtained. This was hydrolyzed, as the crude product, analogously to Example 24. Melting point: 78° to 79° C. (a little ether).

EXAMPLE 28

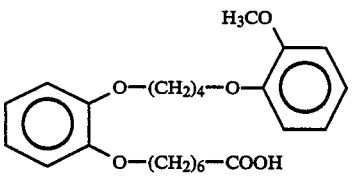

If O-monoacetyl-pyrocatechol was reacted with [(2-methoxy)-4-phenoxy]-butyl bromide analogously to Example 7, the hydrolysis of the acetyl group was carried out as described and the pyrocatechol ether isolated was reacted with 7-bromo-heptanoic acid methyl ester, the methyl ester of the above acid was obtained. This was hydrolyzed, as the crude product, analogously to Example 24. Melting point: 65° to 66° C. (ether).

EXAMPLE 29

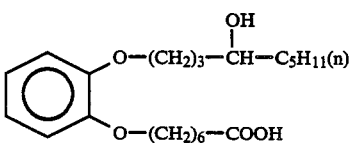

If pyrocatechol 4-hydroxy-nonyl ether (Example 7b)) was reacted with 7-bromo-heptanoic acid methyl ester, the methyl ester of the above acid was obtained.

EXAMPLE 30

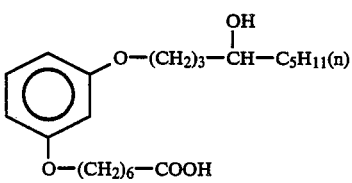

If 4-hydroxy-nonyl resorcyl ether (Example 1b)) was reacted with 7-bromo-heptanoic acid methyl ester, the methyl ester of the above acid was obtained. This was hydrolyzed analogously to Example 24. Melting point: 44° to 45° C. (digested with petroleum ether).

EXAMPLE 31

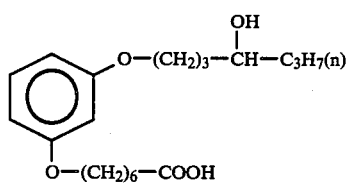

If 4-hydroxy-heptyl resorcyl ether, an intermediate from Example 17, was reacted with 7-bromo-heptanoic acid methyl ester analogously to Example 1, the methyl ester of the above acid was obtained. This was hydrolyzed analogously to Example 24. A non-crystallizing viscous oil was otained.

EXAMPLE 32

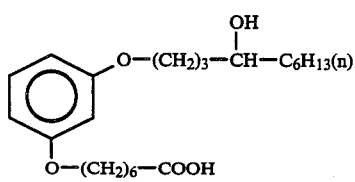

If 4-hydroxy-decyl resorcyl ether, an intermediate from Example 19, was reacted with 7-bromo-heptanoic acid methyl ester analogously to Example 1, the methyl ester of the above acid was obtained. This was hydrolyzed analogously to Example 24. Melting point: 46° C. (digest with petroleum ether).

EXAMPLE 33

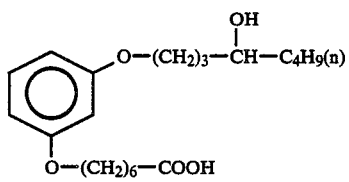

If 4-hydroxy-octyl resorcyl ether, an intermediate from Example 3, was reacted with 7-bromo-heptanoic acid methyl ester, the methyl ester of the above acid was obtained. This was hydrolyzed analogously to Example 24. An oil of boiling point $_{0.01}$ 230° to 231° C. (retort flask with wide cross-sections) was otained.

EXAMPLE 34

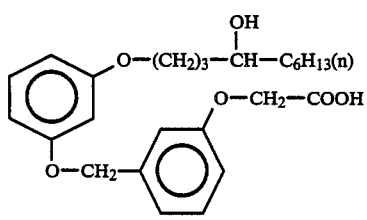

If 4-hydroxy-decyl resorcyl ether, an intermediate from Example 19, was reacted with (3-α-chloromethyl)-phenoxyacetic acid ethyl ester analogously to Example 1, the ethyl ester of the above acid was obtained. This was hydrolyzed analogously to Example 24. A viscous oil was obtained, which was purified over

EXAMPLE 35

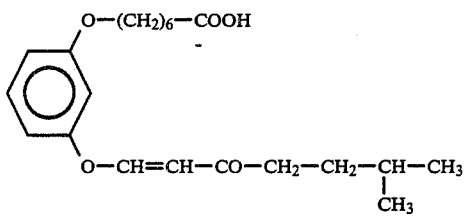

17.7 g of 6-methyl-1-heptin-3-one of boiling point 49° to 53° C. (prepared analogously to Monath. Chem. 108, 659 (1977)) were mixed with 14.4 g of Euresol and 90 ml of methyl ethyl ketone, and 9.5 ml of 40% strength methanolic Triton B solution were added. The mixture was warmed to 65° C., and was subsequently stirred at room temperature for 2 hours. It was then evaporated in vacuo, a little hydrochloric acid was added and the residue was then partitioned between ether and water. The ethereal solution was washed with water, dried over Na$_2$SO$_4$ and evaporated. The evaporation residue was taken up in 100 ml of methanol and the mixture was boiled with a solution of 11.6 g of NaOH in 50 ml of water fro 1 hour. The solution was then evaporated in vacuo, the residue was taken up in water and the aqueous solution was purified by washing with ether. The aqueous solution was then acidified and the resulting 6-methyl-3-oxo-1-(E)-heptenyl resorcyl ether was extracted with diethyl ether. After drying over Na$_2$SO$_4$ and evaporation in vacuo, 9.7 g of evaporation residue were obtained. 1.3 g of NaH (80% in paraffin) and a trace of NaI were added to 9.7 g of 6-methyl-3-oxo-1-(E)-heptenyl resorcyl ether in 100 ml of a 1:1 dimethylformamide/toluene mixture. 9.2 g of 7-bromo-heptanoic acid methyl ester were then added dropwise and the mixture was boiled for 15 hours. After being cooled, the mixture was filtered with suction, the filtrate was evaporated in vacuo, the residue was taken up in ether and the mixture was washed with water. Evaporation of the dried ether extract gave 12.6 g of the crude methyl ester of the above acid.

Hydrolysis of the methyl ester according to Example 24 gave the above acid of melting point 92° to 93° C. (ether/petroleum ether).

Among the new dihydroxybenzene ether derivative salts of the invention, those salts that are pharmaceutically acceptable are particularly important and are preferred.

The new free dihydroxybenzene ether derivatives of the general formula I and their salts can be interconverted in any suitable manner; methods for such interconversion are known in the art.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to an animal or human being is converted in the patient's body to the active compound.

It will be appreciated that the instant specification and examples are set forth by way of illustration and not limitation, and that various modifications and changes may be made without departing from the spirit and scope of the present invention.

We claim:

1. An ether derivative of a dihydroxybenzene of the formula

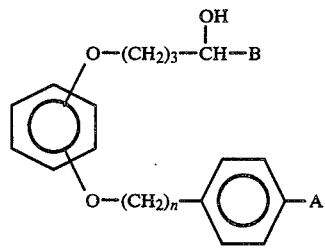

wherein the ether groups are either ortho- or meta- to one another;

A is selected from the group consisting of —COOH, —COOC$_2$H$_5$, —CH=CH—COOH and —CH=CH—COOC$_2$H$_5$;

B is an alkyl radical having from 3 to 6 carbon atoms, and n is 1 to 3, or a pharmaceutically acceptable salt thereof.

2. A compound according to claim 1, wherein such compound is of the formula

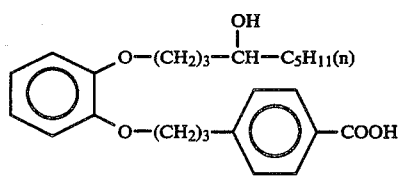

or a pharmacologically acceptable salt thereof.

3. A compound according to claim 1, wherein such compound is of the formula

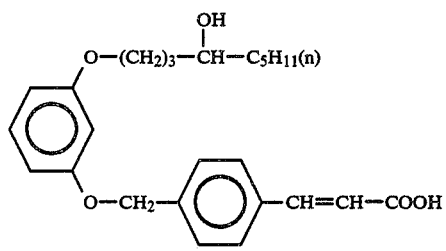

or a pharmacologically acceptable salt thereof.

4. A compound according to claim 1, wherein such compound is of the formula

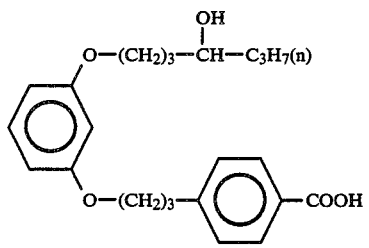

or a pharmacologically acceptable salt thereof.

5. A compound according to claim 1, wherein such compound is of the formula

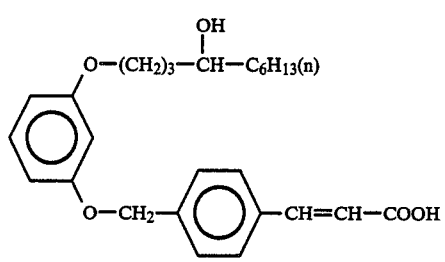

or a pharmacologically acceptable salt thereof.

6. A compound according to claim 1, wherein such compound is of the formula

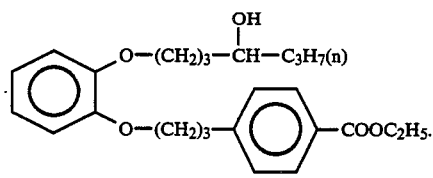

7. A thrombin-inhibitory composition comprising a thrombin-inhibiting effective amount of a compound according to claim 1 in admixture with a diluent.

8. A unit dose of a composition according to claim 7 in the form of a tablet, pill, dragee, capsule, ampoule or suppository.

9. A method of combating cardiac infarctions, angina pectoric, thromboembolic illnesses in the venous and arterial region and arteriosclerosis in human and non-human animals which comprises administering to the animals a thrombin-inhibitory effective amount of a compound according to claim 1.

10. The method according to claim 9, wherein such compound is

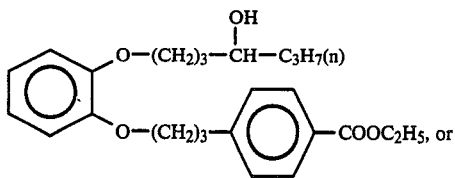

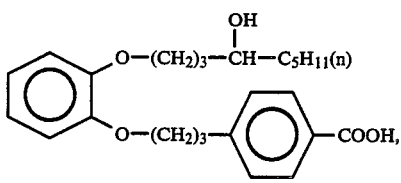

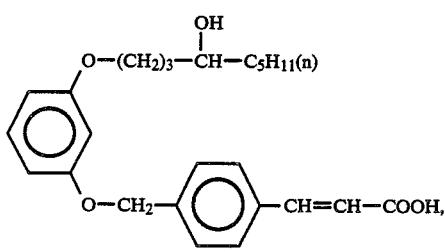

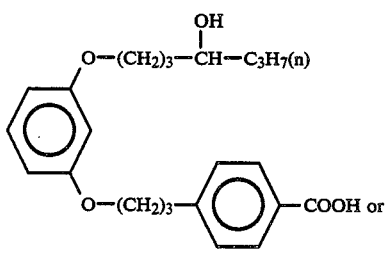

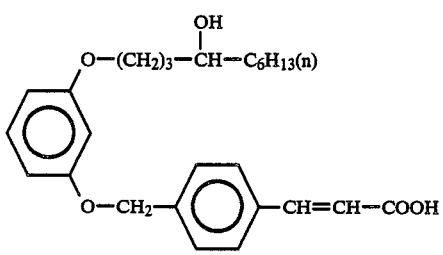

or a pharmacologically acceptable salt thereof.

* * * * *